(12) United States Patent
Jarvas et al.

(10) Patent No.: US 11,747,271 B2
(45) Date of Patent: Sep. 5, 2023

(54) TRIPLE-INTERNAL STANDARD BASED GLYCAN STRUCTURAL ASSIGNMENT METHOD FOR CAPILLARY ELECTROPHORESIS ANALYSIS OF CARBOHYDRATES

(71) Applicant: DH TECHNOLOGIES DEVELOPMENT PTE. LTD., Singapore (SG)

(72) Inventors: Gabor Jarvas, Veszprem (HU); Marton Geza Szigeti, Budapest (HU); Andras Guttman, Brea, CA (US); Jeff Chapman, Santa Ana, CA (US)

(73) Assignee: DH Technologies Development Pte. Ltd., Singapore (SG)

(*) Notice: Subject to any disclaimer, the term of this patent is extended or adjusted under 35 U.S.C. 154(b) by 631 days.

(21) Appl. No.: 16/328,208

(22) PCT Filed: Aug. 17, 2017

(86) PCT No.: PCT/IB2017/054989
§ 371 (c)(1),
(2) Date: Feb. 25, 2019

(87) PCT Pub. No.: WO2018/037316
PCT Pub. Date: Mar. 1, 2018

(65) Prior Publication Data
US 2019/0234867 A1    Aug. 1, 2019

Related U.S. Application Data

(60) Provisional application No. 62/518,104, filed on Jun. 12, 2017, provisional application No. 62/380,062, filed on Aug. 26, 2016.

(51) Int. Cl.
*G01N 21/33*    (2006.01)
*G01N 33/53*    (2006.01)
(Continued)

(52) U.S. Cl.
CPC ......... *G01N 21/33* (2013.01); *G01N 33/5308* (2013.01); *G16C 20/20* (2019.02);
(Continued)

(58) Field of Classification Search
None
See application file for complete search history.

(56) References Cited

U.S. PATENT DOCUMENTS

2013/0007525 A1    3/2013    Rapp et al.
2015/0033834 A1    2/2015    Gundry et al.

FOREIGN PATENT DOCUMENTS

WO    2008057083 A1    5/2008

OTHER PUBLICATIONS

Mittermayr, S. et al. Influence of molecular configuration and conformation on the electromigration of oligosaccharides in narrow bore capillaries, Electrophoresis, vol. 33, pp. 1000-1007 (Year: 2012).*

(Continued)

*Primary Examiner* — Xiaoyun R Xu
(74) *Attorney, Agent, or Firm* — Kasha Law LLC; John R. Kasha; Kelly L. Kasha (57) ABSTRACT

A separation device receives a known or unknown glycan that is co-injected with three different oligomers maltooligosaccharide (MOL). A detector measures the separated glycan and the separated three different oligomers as intensity peaks that are a function of migration time. The migration times of a plurality of other oligomers of MOL are calculated from the migration times of the three different oligomers. Glucose unit (GU) values for the intensity peaks of the separated glycan are calculated by comparing their migration times to the calculated migration times of the plurality of other oligomers of MOL. The processor identifies the structure of the glycan by comparing the calculated (Continued)

GU values of the intensity peaks of the separated glycan to a database of GU values for known glycan structures.

15 Claims, 7 Drawing Sheets

(51) Int. Cl.
    *G16C 20/20*     (2019.01)
    *G01N 21/64*     (2006.01)
    *G01N 27/447*     (2006.01)
    *G01N 30/04*     (2006.01)
    *G01N 30/88*     (2006.01)

(52) U.S. Cl.
    CPC ... *G01N 21/6402* (2013.01); *G01N 27/44726* (2013.01); *G01N 2030/045* (2013.01); *G01N 2030/8836* (2013.01)

(56) References Cited

OTHER PUBLICATIONS

Trbojevic-Akmacic, I et al. High-throughput analysis of immunoglobulin G glycosylation, vol. 13(5), pp. 523-534 (Year: 2016).*
International Search Report and Written Opinion for PCT/IB2017/054989, dated Mar. 16, 2018.
Guttman et al., "Effect of Separation Temperature on Structure Specific Glycan Migration in Capillary Electrophoresis" Analytical Chemistry, 2015, vol. 87, pp. 11630-11634.
Rashid, et al., "Discrimination of Large Maltooligosaccharides from Isobaric Dextran and Pullulan using Ion Mobility Mass Spectrometry" Rapid Communications in Mass Spectrometry, 2014, vol. 28, pp. 191-199.
Jarvas et al. "Triple-Internal Standard Based Glycan Structural Assignment Method for Capillary Electrophoresis Analysis of Carbohydrates" Analytical Chemistry, Nov. 4, 2016, vol. 88, pp. 11364-11467.

* cited by examiner

TRIPLE-INTERNAL STANDARD BASED GLYCAN STRUCTURAL ASSIGNMENT METHOD FOR CAPILLARY ELECTROPHORESIS ANALYSIS OF CARBOHYDRATES

CROSS REFERENCE TO RELATED APPLICATION

This application claims the benefit of U.S. Provisional Patent Application Ser. No. 62/380,062, filed Aug. 26, 2016, and U.S. Provisional Patent Application Ser. No. 62/518,104, filed Jun. 12, 2017, the content of both of which is incorporated by reference herein in its entirety.

INTRODUCTION

The teachings herein relate to identifying the structure of a carbohydrate or any glycan in a sample using separation techniques such as capillary electrophoresis or liquid chromatography. More particularly the teachings herein relate to systems and methods for identifying the structure of a glycan using the co-injection of a triple-internal standard for glucose unit (GU) calculation, which alleviates the need for accompanying runs of a maltooligosaccharide ladder for this calculation. Bracketing standards are co-injected, while the internal standard is part of the sample. The systems and methods herein can be performed in conjunction with a processor, controller, or computer system, such as the computer system of FIG. 1.

Glucose Unit (GU) Calculation

Carbohydrates are among the most structurally diverse biopolymers in nature, thus posing significant analytical challenges. The extremely high diversity of possible glycan structures makes their structural elucidation very difficult even with the most powerful bioanalytical techniques of liquid chromatography (LC), capillary electrophoresis (CE), multicapillary electrophoresis, mass spectrometry (MS), and nuclear magnetic resonance spectroscopy (NMR), or some combinations of them. A glycan is any polysaccharide or oligosaccharide, especially one that is part of a glycoprotein or glycolipid. https://en.wikipedia.org/wiki/Glycan as of Mar. 23, 2017. A carbohydrate is a saccharide, which is a type of glycan or can be a part of a glycan. https://en.wikipedia.org/wiki/Carbohydrate as of Mar. 23, 2017.

LC and CE based glycomics methods are regularly used in the glycoanalytical field. In both techniques, glucose unit (GU) calculation is the prevalent approach for database search based structural assignment. The glucose unit approach is based on the direct comparison of the migration times of unknown analyte peaks with a mixture of increasing size oligosaccharide structures (usually dubbed as "ladder" in the literature) to assist structural elucidation.

In CE or LC, for example, the maltooligosaccharide (MOL) ladder is used for this purpose. The ladder comprises glucose units (such as, but not limited to, α1-4, α1-6, β1-4, β1-6, β, etc. linked units) with their degree of polymerization (DP) ranging from unity up to dozens. CE is an outstandingly powerful separation technique, but without the use of additional analytical dimensions, such as exoglycosidase based degradation assays or mass spectrometry, it does not provide direct structural information unless accompanied by GU calculations relative to glycan structural databases.

However, the accuracy of the GU value calculation strongly depends on the precision of the elution/migration time measurements and practically all liquid phase separation methods suffer from elution/migration time shifts and possible co-elution/migration of different oligosaccharide structures. Conversion of migration times to relative migration times can increase precision. In addition, a priori information about the sample could help to avoid data misinterpretation. The GU approach is aiming to become system-independent, serving as a standard structural elucidation method in glycobiology. Despite its well-established role in the chromatography field, CE based data processing and interpretation is still in its early stages.

Manual GU calculation, in practice, was a time-consuming process before the release of computer programs to perform this task. Some of these computer programs offer excellent multilane CE migration time alignment addressing inter-sample migration time shifts as well as stretching/compression of the electropherograms, but do not address GU value calculation and the subsequent structural assignment.

In a typical CE based GU approach experiment, one or more MOL standard samples are prepared along with each known or unknown glycan sample. A MOL standard sample is separated first using CE. Intensity peaks of the oligomers are detected using a detector connected to the CE device. Methods of detection employed by the detector can include, but are not limited to, fluorescence detection, ultraviolet light detection, or mass spectrometry. The intensity peaks of the oligomers detected from the MOL standard sample are measured as a function of migration time.

After separating the MOL standard sample, a known or unknown glycan sample is separated using the same CE device. Intensity peaks of the known or unknown glycan sample are also measured as a function of migration time.

Figure 2:
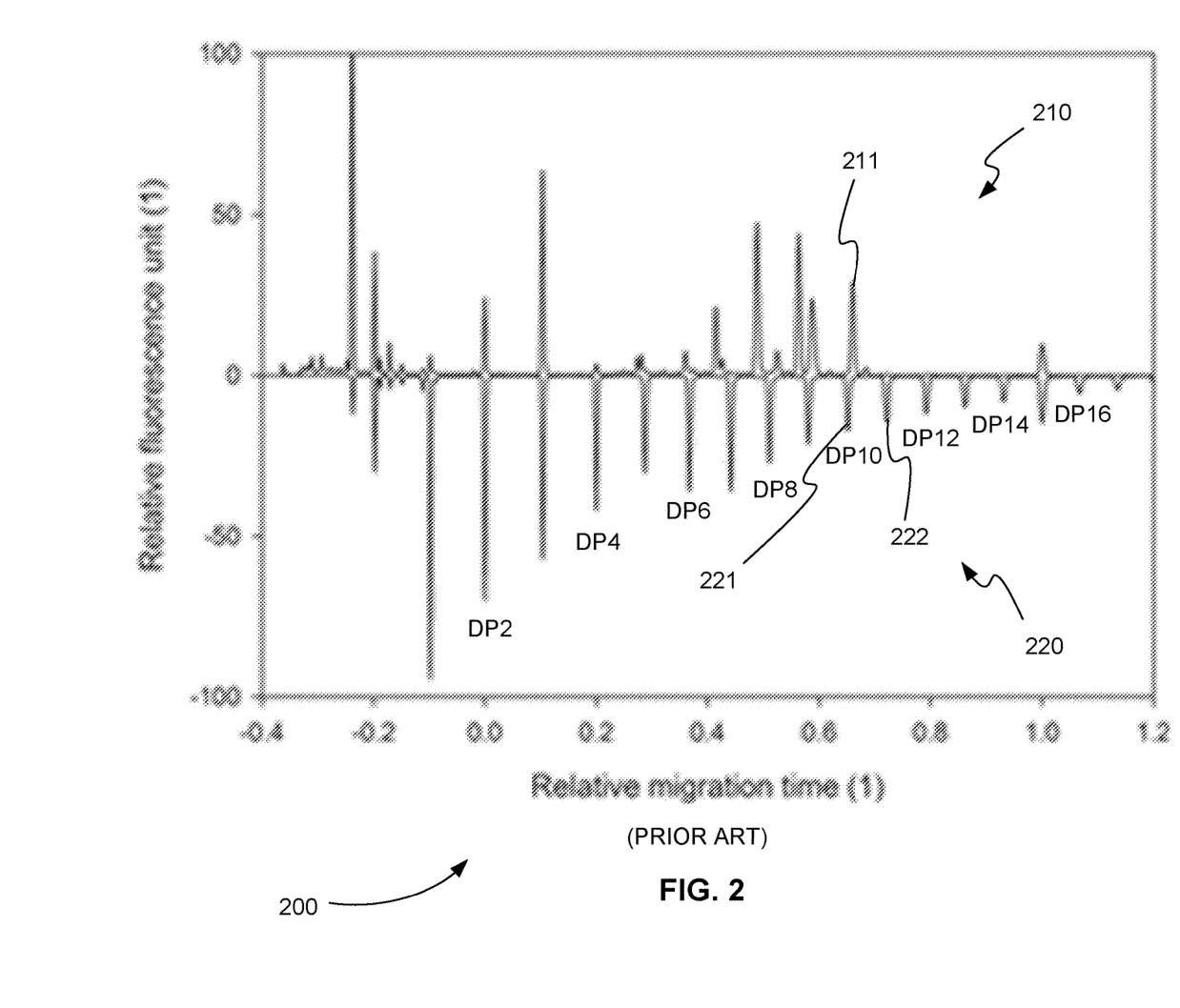
FIG. 2 is an exemplary plot or electropherogram showing a comparison of the intensity peaks of a known 8-amino-pyrene-1,3,6-trisulphonic acid (APTS) labeled human immunoglobulin G (IgG) N-glycan and a maltooligosaccharide (MOL) standard ladder demonstrating the alignment of peaks on the relative migration time basis.

FIG. 2 is an exemplary plot or electropherogram 200 showing a comparison of the intensity peaks of known 8-aminopyrene-1,3,6-trisulphonic acid (APTS) labeled human immunoglobulin G (IgG) N-glycans and a maltooligosaccharide (MOL) standard ladder demonstrating the alignment of peaks on the relative migration time basis. Intensity peaks 210 of the known IgG N-glycans are shown in the upper trace, and intensity peaks 220 of the MOL standard ladder are shown in the lower trace. Intensity peaks 210 and 220 are shown in the same plot 200 for comparison purposes. Intensity peaks 210 and 220 were obtained from separate CE experiments using the same CE device.

In a typical CE based GU experiment the migration times of the intensity peaks of the known or unknown glycan are compared to the migration times of the intensity peaks of the MOL standard to identify the glycan. In particular, the peaks are compared to determine the relative distance in time from a peak of the known or unknown glycan to a peak or α1-4 linked glucose unit of the MOL standard ladder. This relative correspondence of a peak of the known or unknown glycan with a peak or α1-4 linked glucose unit of the MOL standard ladder determines the degree of polymerization (DP) of the known or unknown glycan ranging from unity up to dozens. The GU value is then expressed in terms of the DP.

For example, the migration times of peaks 210 of the known IgG N-glycans are compared to peaks 220 of the MOL standard ladder to determine a relative GU value for each of peaks 210 of the known IgG N-glycans. Once the GU values for peaks 210 of the known IgG N-glycans are obtained, these GU values are compared to a glycan structural database that includes reference GU values for a plurality of glycans. From matching the calculated GU values to the reference GU values of the glycan structural database, the structure of known IgG N-glycan is confirmed.

In order to achieve maximum precision and avoid drifting migration times on single spectral imaging detection systems, GU value calculation requires the run of an accompanying MOL ladder for each sample, which doubles sample processing time. In some cases, a MOL standard ladder experiment is performed before and after the experiment on the known or unknown glycans. As a result, three separate separation experiments are performed, tripling the sample processing time.

Alternatively, a single MOL ladder can be used for a batch of samples. However, in this scenario, the series of runs may have slightly different separation conditions resulting migration time shifts. This alteration is most likely caused by the variance in capillary wall coverage, i.e., coating issues and/or adsorbed analyte molecules, background electrolyte components, or impurities. Minor migration time shifts have been observed between the uncoated and coated capillaries that did not affect GU values.

With a single color detection system, co-injection of the MOL ladder with the sample has no practical relevance since several of the ladder and sample peaks could overlap. In multispectral imaging (i.e., using multiple wavelengths to detect differently labeled species at the same time), co-injection of the ladder could cause displacement effects the peaks of interest, thus making data evaluation ambiguous.

Because at least one, and often two, separate MOL standard ladder separation experiments are performed for each known or unknown glycan separation experiment, the traditional LC or CE based GU experiment can be time-consuming. In addition, these experiments are expensive in terms of laboratory materials and resources, because as many as three experimental samples must be created and analyzed for each known or unknown glycan. For example, two-thirds of a 96 well plate may be used to contain just the MOL standard ladder samples.

In addition, traditional LC or CE based GU experiments require comparisons among separate experiments performed on the same device. These are the comparisons among results from the known or unknown glycan experiment and one or two MOL standard ladder experiments. Consequently, additional error can be introduced in the setup and measurement of different experiments.

As a result, there is a need for improved methods of performing LC or CE based GU experiments that can (1) reduce the amount of time required for these experiments (2) decrease the cost of these experiments, and (3) improve the accuracy of these experiments.

SUMMARY

A system, method, and computer program product are disclosed for identifying the structure of a glycan by co-injecting with the glycan a triple internal standard made up of three different oligomers of maltooligosaccharide (MOL). All three embodiments include the following steps.

A separation device receives a known or unknown glycan that is co-injected with three different oligomers of MOL. In a preferred embodiment, the three different oligomers of MOL are glucose $\alpha$1-4 oligomers. However, these oligomers of MOL can be any other sugar, or any other molecule that migrates around the same time. Two of the three the oligomers of MOL are the bracketing standards, and one is the internal labeling standard that is also used for the calculation of other oligomers of MOL, which creates a virtual ladder of oligomer migration times.

The separation device separates the glycan and the three different oligomers over time. A detector measures the separated glycan and the separated three different oligomers as intensity peaks that are a function of migration time.

A processor receives the intensity peaks of separated glycan and the separated three different oligomers. The processor calculates the migration times of a plurality of other oligomers of MOL from the migration times of the three different oligomers. The processor calculates glucose unit (GU) values for the intensity peaks of the separated glycan by comparing their migration times to the calculated migration times of the plurality of other oligomers of MOL. The processor identifies the structure of the glycan by comparing the calculated GU values of the intensity peaks of the separated glycan to a database. The database includes GU values for known glycan structures. The structure of the glycan is found from the matching structures of the database.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

Figure 1:
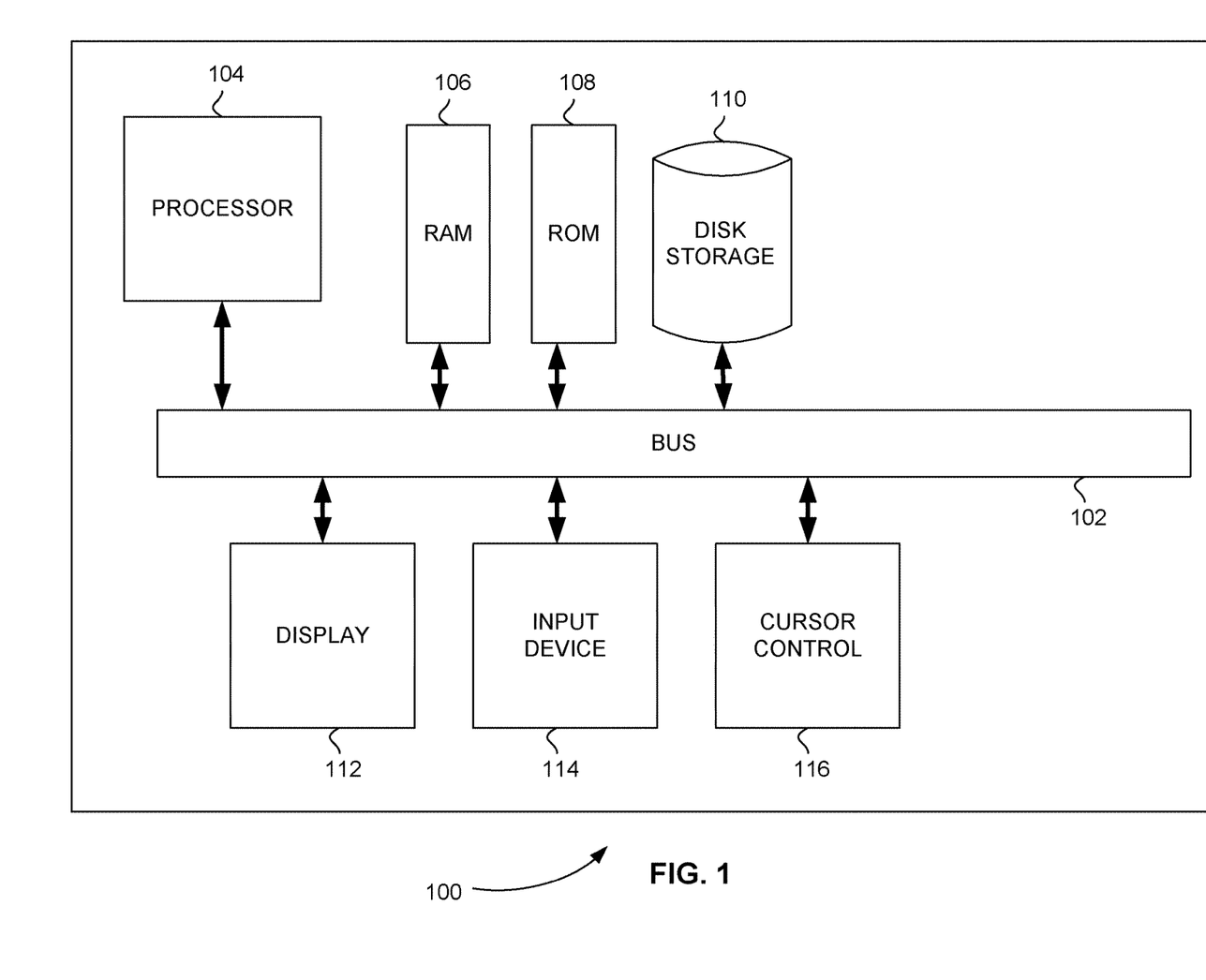
FIG. 1 is a block diagram that illustrates a computer system, upon which embodiments of the present teachings may be implemented.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively, hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Electroporetic Systems and Methods

Electrophoretic methods are used to facilitate the detection of target analytes. Such methods exploit the fact that molecules in solution have an intrinsic electrical charge. Thus, in the presence of an electric field, each molecular species migrates with a characteristic "electrophoretic" mobility which is dependent upon the mass to charge ratio of the molecular species. When this ratio is different from among the various species present, they separate from one another. Under the influence of such a field, all of the variants will move toward a designated charge opposite to the charge of the variants; those having a lower electrophoretic mobility will move slower than, and hence be separated from, those having a (relative) higher electrophoretic mobility.

Electrophoresis has been used for the separation and analysis of mixtures. Electrophoresis involves the migration and separation of molecules in an electric field based on differences in mobility. Various forms of electrophoresis are known, including free zone electrophoresis, gel electrophoresis, isoelectric focusing, and isotachophoresis. Another form, capillary electrophoresis (CE), is directed to the separation of free and bound label. In general, CE involves introducing a sample into a capillary tube, i.e., a tube having an internal diameter of from about 2 pm to about 2000 um (preferably, less than about 50 um; most preferably, about 25 pm or less) and applying an electric field to the tube (Chen, F-T. A., J. Chromatogr. 516:69*78 (1991); Chen, F-T. A., et al., J. Chromatogr. 15:1143*1161 (1992)). Since each of the sample constituents has its own individual electrophoretic mobility, those having greater mobility travel through the capillary tube faster than those with slower mobility. Hence, the constituents of the sample are resolved into discrete zones in the capillary tube during their migration through the tube. The method is well suited to automation, since it provides convenient on-line injection, detection, and real-time data analysis.

Figure 3:
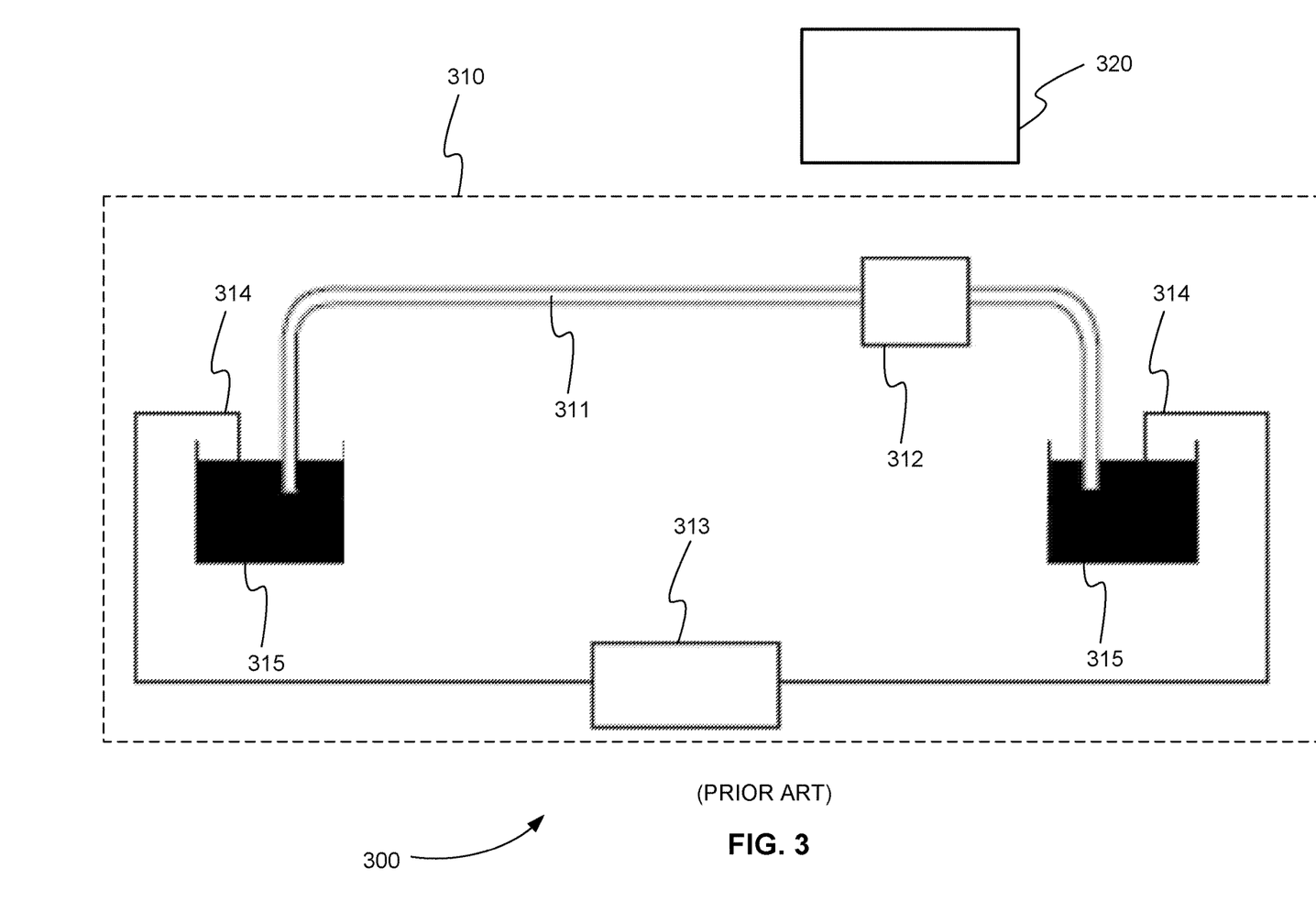
FIG. 3 is an exemplary CE system.

FIG. 3 is an exemplary CE system 300. CE system 300 includes CE device 310 and detector 320. CE device 310 includes fused-silica capillary 311 with optical viewing window 312, controllable high voltage power supply 313, two electrode assemblies 314, and two buffer reservoirs 315. The ends of capillary 311 are placed in the buffer reservoirs and optical viewing window 312 is aligned with detector 320, when detector 320 is an optical detector. After filling capillary 311 with buffer, the sample can be injected into capillary 311.

Electrophoresis is fundamentally the movement of charged particles within an applied electric field. In CE, a sample is injected at one end of capillary 311. Detector 320 is positioned or attached to capillary 311 at the other end of capillary 311 distant from the sample. A voltage, provided by high voltage power supply 313 and two electrode assemblies 314, is applied along the length of the capillary 311.

With the electric potential applied, two separate flow effects occur. The first of these flow effects is a gross sample flow effect. The sample moves as a mass into the capillary. The second of these flow effects is the electrophoretic flow. This causes the constituents of the sample having differing electric charges to move relative to the main stream of fluid within capillary 311. The portions of the sample having differing electric charges are thereby separated in capillary 311.

Different detectors may be used to analyze the sample after the electrophoretic separation has occurred. These detectors can include, but are not limited to, an ultraviolet (UV) detector, a laser-induced fluorescence (LIF) detector, or a mass spectrometer. A UV detector, for example, is used to measure the amount of UV light absorbed by the separated sample. An LIF detector, for example, is used to provide a high-sensitivity measurement of labeled molecular species.

In a system that combines capillary electrophoresis with electrospray ionization (ESI) and mass spectrometry (MS), the output of the capillary is input to an electrospray assembly. The electrospray ionization is accomplished by placing a high voltage potential at the outlet of the separation capillary with respect to the capillary inlet to the mass spectrometer. The separation capillary also requires a high voltage potential placed between its inlet and outlet. The separated portions of the sample are dispersed by the electrospray into a fine aerosol as they exit the capillary. The droplets of the aerosol are then observed by mass spectrometry.

Compared to the early developmental instruments, fully automated CE devices offer computer control of all operations, pressure and electrokinetic injection, an autosampler and fraction collector, automated methods development, precise temperature control, and an advanced heat dissipation system. Automation is critical to CE since repeatable operation is required for precise quantitative analysis.

Systems and Methods for Performing a Triple-Internal Standards GU Experiment

As described above, liquid chromatography (LC), capillary electrophoresis (CE), and multicapillary electrophoresis based glycomics methods are regularly used in the glycoanalytical field to determine the structure of glycans. In both techniques, glucose unit (GU) calculation is the prevalent approach for database search based structural assignment. The glucose unit approach is based on the direct comparison of the migration times of unknown analyte peaks with a mixture of increasing size oligosaccharide structures called a ladder. In CE or LC, for example, the maltooligosaccharide (MOL) ladder is used for this purpose.

In a typical CE based GU approach experiment, one or more MOL standard samples are prepared along with each known or unknown glycan sample. A MOL standard sample is separated first using CE. Intensity peaks of the oligomers are detected using a detector connected to the CE device. The intensity peaks of the oligomers detected from the MOL standard sample are measured as a function of migration time.

After separating the MOL standard sample, a known or unknown glycan sample is separated using the same CE device. Intensity peaks of the known or unknown glycan sample are also measured as a function of migration time.

As described above, FIG. 2 shows a comparison of the intensity peaks of a known 8-aminopyrene-1,3,6-trisulphonic acid (APTS) labeled human immunoglobulin G (IgG) N-glycan and a maltooligosaccharide (MOL) standard ladder demonstrating the alignment of peaks on the relative migration time basis. Intensity peaks 210 of the known IgG N-glycan are shown in the upper trace, and intensity peaks 220 of the MOL standard ladder are shown in the lower trace.

In a typical CE based GU experiment the migration times of the intensity peaks of the known or unknown glycan are compared to the migration times of the intensity peaks of the MOL standard to identify the glycan. Referring to FIG. 2, the migration times of peaks 210 of the known IgG N-glycan are compared to peaks 220 of the MOL standard ladder to determine a relative GU value for each of peaks 210 of the known IgG N-glycan.

For example, the GU value of peak 211 of the known IgG N-glycan can be calculated from $$GU_x = G_n + (t_x - t_n)/(t_{n+1} - t_n) \qquad (1),$$

where $GU_x$ is the GU value of the unknown oligosaccharide, $G_n$ is the degree of polymerization (DP) of the preceding MOL standard ladder peak, $t_x$ is the migration time of the unknown oligosaccharide, and $t_{n+1}$ and $t_n$ are the migration times of the MOL standard ladder peaks following and preceding the peak of the unknown oligosaccharide. The DPs of the preceding and following MOL standard ladder peaks are expressed as an integers, which represent the corresponding rungs of the ladder.

Referring again to FIG. 2, the preceding MOL standard ladder peak of peak 211 is peak 221. The DP of peak 221 is DP10, so $G_n$ is 10. The relative migration time, $t_x$, of the unknown oligosaccharide, or peak 211, is 0.66. The migration time, $t_n$, of the preceding MOL standard ladder peak 221 is 0.65. The migration time, $t_{n+1}$, of the following MOL standard ladder peak 222 is 0.72. As a result, the GU value of peak 211, GUI, is 10+(0.66−0.65)/(0.72−0.65), or 10.143.

Once the GU values for peaks 210 of the known IgG N-glycan are obtained, these GU values are compared to a glycan structural database that includes reference GU values for a plurality of glycans. For example, the GU value of peak 211, 10.143, is compared to the GU values for a plurality of glycans in a glycan structural database. From matching the calculated GU values to the reference GU values of the glycan structural database, the structure of known IgG N-glycan is confirmed. In this case, the IgG N-glycan is known, so its structure is confirmed. If the glycan is unknown, the matching structure from the glycan structural database identifies the structure of the unknown glycan.

As described above, because at least one, and often two, separate MOL standard ladder separation experiments are performed for each known or unknown glycan separation experiment, the traditional LC or CE based GU experiment can be time-consuming and expensive in terms of laboratory materials and resources. In addition, traditional LC or CE based GU experiments require comparisons among separate experiments performed on the same device, which can introduce additional error in the measurements.

As a result, there is a need for improved methods of performing LC or CE based GU experiments that can (1) reduce the amount of time required for these experiments (2) decrease the cost of these experiments, and (3) improve the accuracy of these experiments.

Co-Injection of Just Three Oligomers of the MOL Standard

In various embodiments, in just one LC or CE separation experiment, only three oligomers of the MOL standard are co-injected with the known or unknown glycan sample in order to obtain the measurements needed for the GU calculations. For example, three α1-4 oligomers can used. However, the three oligomers could be any other sugar, linkage or even non sugar molecules. Using the measurements from just three oligomers of the MOL standard prevents the overlap or interference of the ladder peaks with the peaks of the known or unknown glycan that was described above. In addition, from just three oligomers of the MOL standard the entire MOL standard ladder can be calculated and used in the GU calculations for the known or unknown glycan.

This ability to use just one separation experiment (1) reduces the amount of time required for a GU experiment (2) decreases the cost of the experiment, and (3) improves the accuracy of the results of the experiment over the traditional method described above.

Analyzing a large number of CE runs, it was observed that the ratio distribution of migration time increments of consecutive peaks was apparently constant. This observation was based on 500+ measured data points including dedicated experiments with altered separation voltage, temperature, capillary type (uncoated and coated), capillary length, injection methods, as well as day to day repetition and instrument dependency investigation.

More specifically, it was observed that the ratio of the migration time difference between two MOL standard ladder peaks and the migration time difference between the next two MOL standard ladder peaks is a constant. For example, it was observed that the ratio of $\Delta t_{2-3}/\Delta t_{3-4}$ and $\Delta t_{3-4}/\Delta t_{4-3}$ equals the same constant, where $\Delta t_{2-3}=t_3-t_2$ is the migration time difference between DP2 and DP3 peaks, $\Delta t_{3-4}=t_4-t_3$ is the migration time difference between DP3 and DP4 peaks, and $\Delta t_{4-3}=t_5-t_4$ is the migration time difference between DP4 and DP5 peaks. Another way of describing this relationship is that the time difference between consecutive MOL standard ladder peaks varies linearly.

Further, it was observed that the ratio of time differences was a different constant in two separate but connected regions. Another way of describing this relationship is that time difference between consecutive MOL standard ladder peaks is linear in two separate but connected regions. There are two separate but connected linear regions, because the migration behavior changes when the sugar oligomer forms a full helical turn at DP>7. This change results in a shift in the calculated migration times at DP>7.

Figure 4:
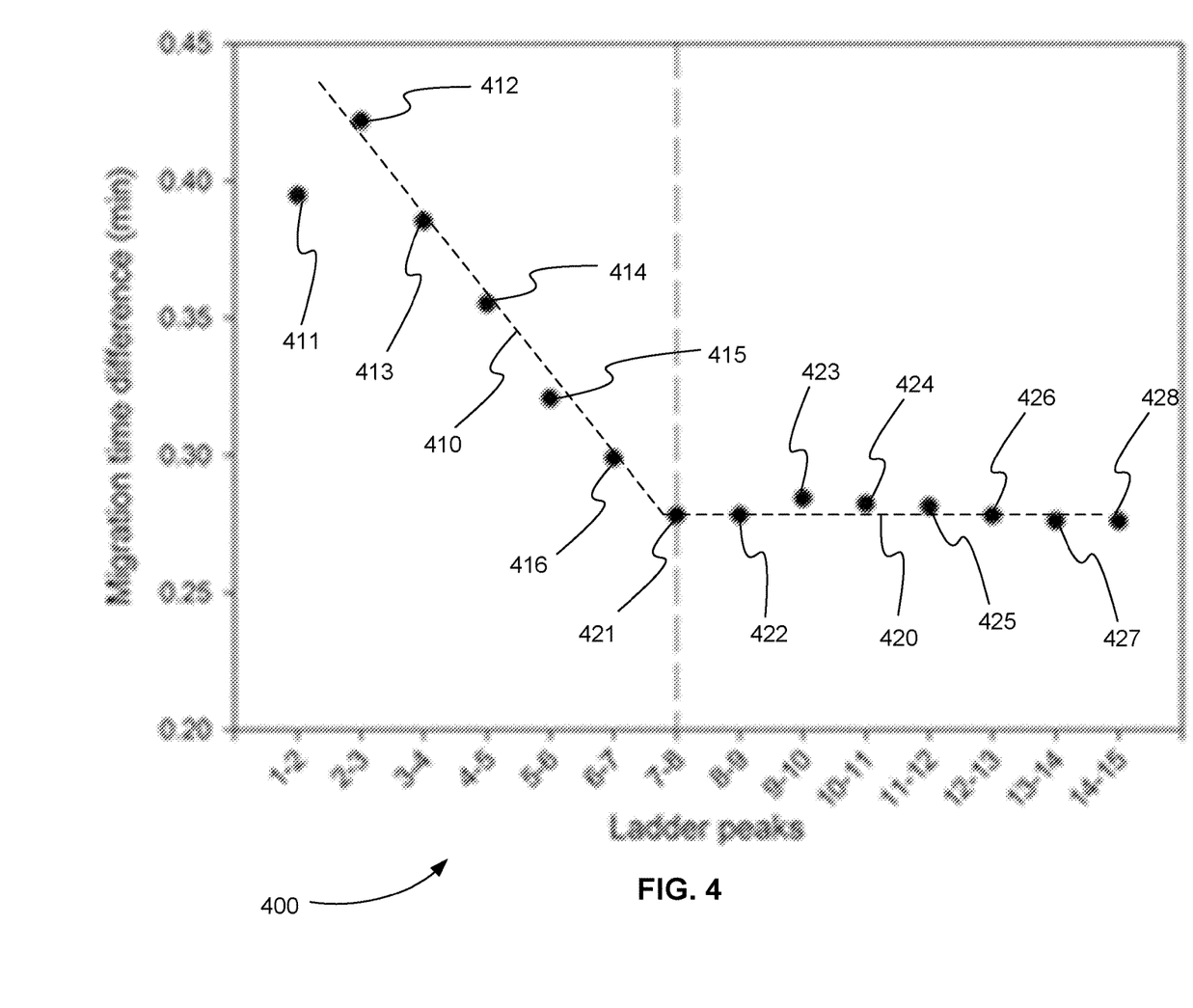
FIG. 4 is an exemplary plot of the migration time differences of consecutive MOL standard ladder peaks versus the consecutive MOL standard ladder peak differences, in accordance with various embodiments.

FIG. 4 is an exemplary plot 400 of the migration time differences of consecutive MOL standard ladder peaks versus the consecutive MOL standard ladder peak differences, in accordance with various embodiments. Plot 400 shows essentially two separate linear regions depicted by lines 410 and 420. The migration time difference point 411 between MOL standard ladder peaks 1-2 is not used. This is because the first oligomers of the MOL standard is not used, because its structure is not equivalent to the other oligomers of the MOL standard. For example, it is not a ring structure.

Excluding migration time difference point 411, therefore, there are two linear regions, lines 410 and 420. The points in each linear region can be calculated from a difference between two measured ladder peak migration times and the observed ratio. As a result, for each of two separate linear regions, two measured ladder peak migration times are needed. In other words, a total of four measured ladder peak migration times is needed.

However, in this case, the two linear regions are not completely separate. They share the DP7 peak. As a result, two measured peak migration times in one region allow the migration time of the DP7 peak to be calculated. With the migration time of the DP7 peak already calculated, only one other migration time needs to be measured in the other region. As a result, a total of only three measured ladder peak migration times is needed to calculate all the points of plot 400 or all the migration times of the entire MOL standard ladder.

In a preferred embodiment, for example, maltose, maltotriose, and maltopentadecaose of the MOL standard are co-injected with a known or unknown glycan. Maltose (lower bracketing standard) and maltotriose (internal standard) provide measurable peaks for one linear region of the MOL standard and maltopentadecaose (upper bracketing s standard) provides a measurable peak for the other linear region. These three separate standards correspond to DP2, DP3, and DP15 of the MOL standard ladder, respectively.

Maltose (DP2) and maltotriose (DP3) are chosen, for example, because they migrate earlier than most other glycan peaks of interest, and maltopentadecaose (DP15) migrates later than most other glycan peaks of interest. As a result, choosing these three particular standards avoids the potential overlap or interference with peaks of the co-injected glycan of interest, which is described above.

From the measured peaks of maltose, maltotriose, and maltopentadecaose (DP2, DP3, and DP15, respectively) the migration times of the entire MOL standard ladder is calculated. For example and referring to FIG. 4, from the measured peaks DP2 and DP3, the migration time difference of these peaks, $\Delta t_{2-3}=t_3-t_2$, is found to be 0.425 min. This is shown as point 412 in FIG. 4. The observed ratio of $\Delta t_{2-3}/\Delta t_{3-4}$ is known to be 1.091. From $\Delta t_{2-3}$ and the observed ratio of 1.091, the migration time difference of peaks DP3 and DP4, $\Delta t_{3-4}$, is found to be 0.390 min. This is shown as point 413 in FIG. 4. Similarly, this is repeated for $\Delta t_{3-4}/\Delta t_{4-5}$. This ratio is also 1.091. As a result, $\Delta t_{4-5}$ is calculated from $\Delta t_{3-4}/1.091$ and is found to be 0.357. In this way, points 412 through 416 of FIG. 4 are calculated as 0.425, 0.390, 0.357, 0.327, and 0.300 min, respectively.

The individual migration times of the ladder peaks can be calculated from the measured migration times of peaks DP2 and DP3 and the calculated migration time differences (points 412 through 416). For example, if the measured migration time of DP2 is 4.323 min and DP3 is 4.748, then the calculated migration times of DP4, DP5, DP6, and DP7 are 5.138, 5.495, 5.822, and 6.122 min, respectively.

Similarly, from the calculated migration time of the DP7, the measured migration time of the DP15, and the observed ratio of migration time differences in the second region of the MOL standard ladder, the remaining points of FIG. 4 and the remaining migration times of the MOL standard ladder are calculated. For example, the migration time of DP15 is measured to be 8.322 min, the migration time of DP7 is calculated to be 6.122 min, and the observed ratio of migration time differences in the second region of the MOL standard ladder is 1.000.

The migration times of DP15 and DP7 are known, so the migration time difference $\Delta t_{7\text{-}15} = t_{15} - t_{17}$ is known. This difference can be expressed as $$\Delta t_{7\text{-}15} = \Delta t_{7\text{-}8} + \Delta t_{8\text{-}9} + \Delta t_{9\text{-}10} + \Delta t_{10\text{-}11} + \Delta t_{11\text{-}12} + \Delta t_{12\text{-}13} + \Delta t_{13\text{-}14} + \Delta t_{14\text{-}15}. \quad (2)$$

It is also known that $$\Delta t_{7\text{-}8}/\Delta t_{8\text{-}9} = \Delta t_{8\text{-}9}/\Delta t_{9\text{-}10} = \Delta t_{9\text{-}10}/\Delta t_{10\text{-}11} = \Delta t_{10\text{-}11}/\Delta t_{11\text{-}12} = \Delta t_{11\text{-}12}/\Delta t_{12\text{-}13} = \Delta t_{12\text{-}13}/\Delta t_{13\text{-}14} = \Delta t_{13\text{-}14}/\Delta t_{14\text{-}15} = K_{ratio}, \quad (3)$$

where $K_{ratio}$ is the known observed ratio 1.000. From these two equations, all of the remaining unknown migration times can be calculated. For example, Equation (2) can be expressed in terms of $\Delta t_{7\text{-}8}$ using Equation (3). Then, Equation (2) becomes $$\Delta t_{7\text{-}15} = \Delta t_{7\text{-}8} + \Delta t_{7\text{-}8}/K_{ratio} + \Delta t_{7\text{-}8}/(K_{ratio})^2 + \Delta t_{7\text{-}8}/(K_{ratio})^3 + \Delta t_{7\text{-}8}/(K_{ratio})^4 + \Delta t_{7\text{-}8}/(K_{ratio})^5 + t_{7\text{-}8}/(K_{ratio})^6 + \Delta t_{7\text{-}8}/(K_{ratio})^7. \quad (4)$$

In Equation (4), $t_7$, $t_{15}$, and $K_{ratio}$ are all known, so the equation can be used to solve for $t_8$. From $t_8$, $\Delta t_{7\text{-}8}$ can be calculated and using Equation (3) all other migration times and migration time differences can be found. In this way, points 421 through 428 of FIG. 4 are calculated as 0.275.

The individual migration times of the ladder peaks can be calculated from the calculated migration times of peaks DP7 and DP8 and the calculated migration time differences (points 422 through 428). For example, if the calculated migration time of DP7 is 6.122 min and DP8 is 6.397, then the calculated migration times of DP9 through DP14 are 6.672, 6.947, 7.222, 7.497, 7.772, and 8.047 min, respectively.

In summary, in a preferred embodiment, maltose (DP2) and maltotriose (DP3) standards from the region ≥DP2 and ≤DP7 and the maltopentadecaose (DP15) standard from the region ≥DP7 are co-injected with a known or unknown glycans in order to calculate the entire MOL standard ladder. In various other embodiments, any two standards from the region ≥DP2 and ≤DP7 and any one standard from the region ≥DP7 can be co-injected with a known or unknown glycan to calculate the entire MOL standard ladder. In this case DP2 and DP15 are the bracketing standards, and DP3 is the internal labeling standard that is also used for the calculation of the virtual ladder.

Also, in various other embodiments, any one standard from the region ≥DP2 and ≤DP7 and any two standards from the region ≥DP7 can be co-injected with a known or unknown glycan to calculate the entire MOL standard ladder. For example, the maltose (DP2) standard from the region ≥DP2 and ≤DP7 and the maltotetradecaose (DP14) and maltopentadecaose (DP15) standards from the region ≥DP7 are co-injected with a known or unknown glycan in order to calculate the entire MOL standard ladder.

In other words, any three oligomer standards from the MOL standard can be used to calculate the entire MOL standard ladder so long as two standards produce peaks in one of two regions of the MOL standard ladder and the third standard produces a peak in the other region. The two regions of the MOL standard ladder are (1) the region between ≥DP2 and ≤DP7 and (2) the region ≥DP7. Of course, the three standards should also be selected to avoid overlap or interference with the known or unknown glycan of interest.

Once the MOL standard ladder peaks are calculated from the measured peaks of the three co-injected standards, the structure of the known or unknown glycan is found by comparing the measured intensity peaks of the known or unknown glycan to the calculated or "virtual" MOL standard ladder peaks. This comparison follows the method described above.

For example, a GU value is calculated for each peak of the known or unknown glycan using Equation (1), shown above. Once the GU values for the peaks of the known or unknown glycan are obtained, these GU values are compared to a glycan structural database that includes reference GU values for a plurality of glycans. From matching the calculated GU values to the reference GU values of the glycan structural database, the structure of the known or unknown glycan is confirmed or identified, respectively.

System for Identifying a Glycan

Figure 5:
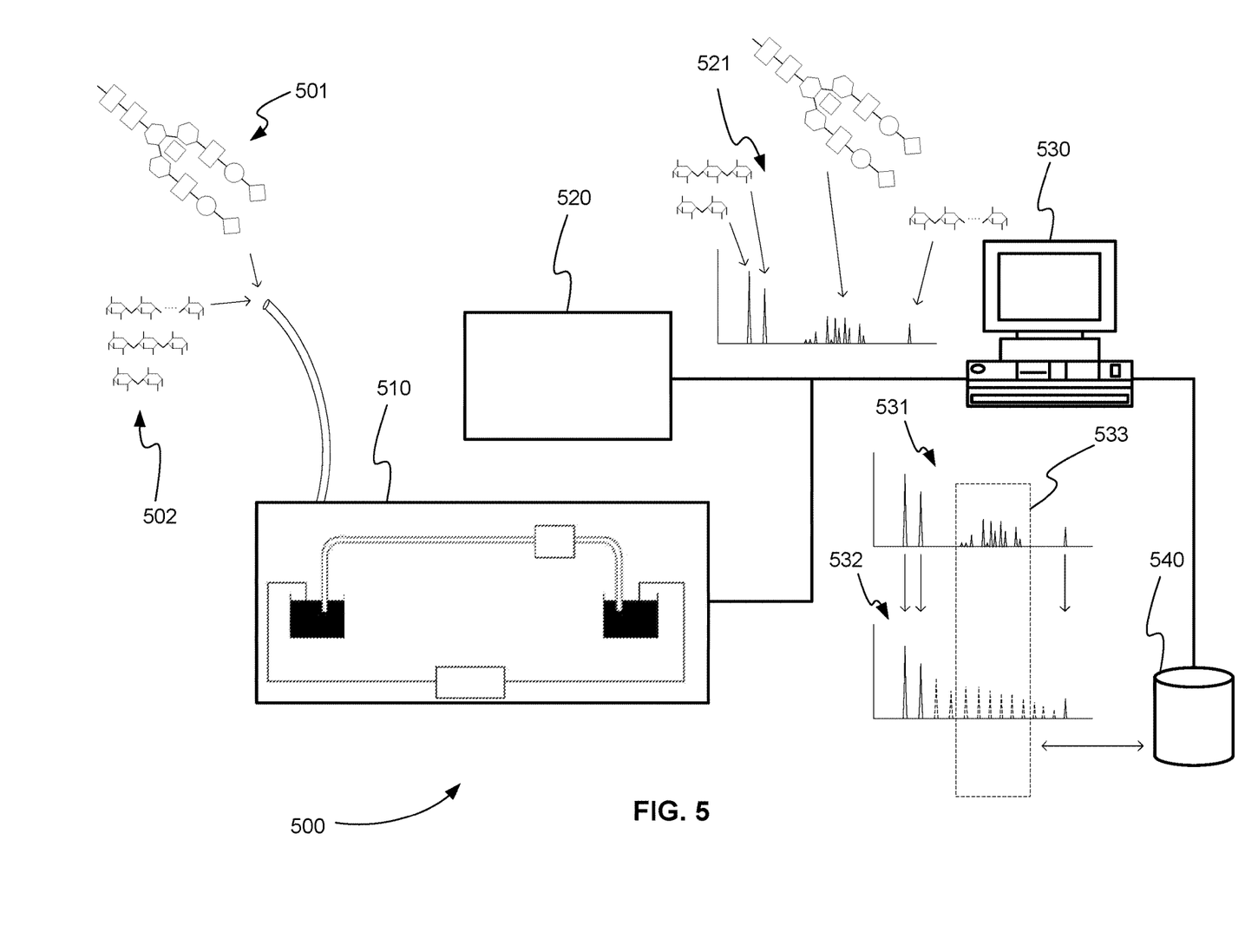
FIG. 5 is a schematic diagram of system for identifying the structure of a glycan by co-injecting with the glycan a triple internal standard made up of three different oligomers of MOL, in accordance with various embodiments.

FIG. 5 is a schematic diagram of system 500 for identifying the structure of a glycan by co-injecting with the glycan a triple internal standard made up of three different oligomers of MOL, in accordance with various embodiments. System 500 includes separation device 510, detector 520, and processor 530.

Separation device 510 can be, but is not limited to, a CE device or an LC device. Separation device 510 receives a known or unknown glycan 501 that is co-injected with three different oligomers 502 of MOL. Separation device 510 separates glycan 501 and the three different oligomers 502 over time.

In a preferred embodiment, the three different oligomers 502 of MOL are glucose α1-4 oligomers. However, any oligomers of MOL can be used, regardless of the monosaccharide type (e.g. galactose, mannose, etc) linkage type (1-6, 1-2, etc) and anomericity (e.g. beta) or any other molecules with similar migration times.

MOL includes oligomers that have a degree of polymerization (DP) ranging from unity up to dozens. The ratio of the difference in migration time between two consecutive oligomers of MOL and the difference in migration time between adjacent consecutive glucoses units of MOL is a first known constant value in a first region of the DP range of MOL and a second known constant value in a second region of the DP range of MOL. Two of the three different oligomers 502 are selected to produce migration times in one of the first region or the second region. The third of the three different oligomers 502 is selected to produce a migration time in the other of the first region or the second region.

In various embodiments, the three different oligomers of MOL includes maltose (lower bracketing standard), maltotriose (internal standard), and maltopentadecaose (upper bracketing standard).

In various embodiments, the first region of the DP range of MOL comprises DP values ≥DP2 and ≤DP7 and the second region of the DP range of MOL comprises DP values ≥DP7.

In various embodiments, two of the three different oligomers 502 are selected to produce migration times in the first region. The third of the three different oligomers 502 is selected to produce a migration time in the second region. In an alternative embodiment, this situation is reversed. Two of the three different oligomers 502 are selected to produce migration times in the second region. The third of the three different oligomers 502 is selected to produce a migration time in the first region.

Detector 520 can be, but is not limited to, an LIF detector, an UV light detector, or a mass spectrometer. If detector 520 is an LIF detector, then glycan 501 and the three different oligomers 502 are labeled for LIF before co-injection.

Detector 520 measures the separated glycan 501 and the separated three different oligomers 502 as intensity peaks that are a function of migration time. These measurements are shown in plot 521, for example.

Processor 530 can be, but is not limited to, a computer, a microcontroller, a microprocessor, the computer system of FIG. 1, or any device capable of sending and receiving control signals and data and processing data. Processor 530 is in communication with separation device 510, detector 520, and database 540.

Processor 530 receives the intensity peaks of separated glycan 501 and the separated three different oligomers 502. Processor 530 calculates the migration times of a plurality of other oligomers of MOL from the migration times of the three different oligomers 502 and the first known constant value and the second known constant value. Plots 531 and 532 depict this calculation.

Processor 530 calculates GU values for the intensity peaks of the separated glycan 501 by comparing their migration times to the calculated migration times of the plurality of other oligomers of MOL. Box 533 highlights the migration times compared in this calculation. Processor 530 identifies the structure of glycan 501 by comparing the calculated GU values of the intensity peaks of separated glycan 501 to database 540. Database 540 includes GU values for known glycan structures. The structure of glycan 501 is found from the matching structures of database 540.

Method for Identifying a Glycan

Figure 6:
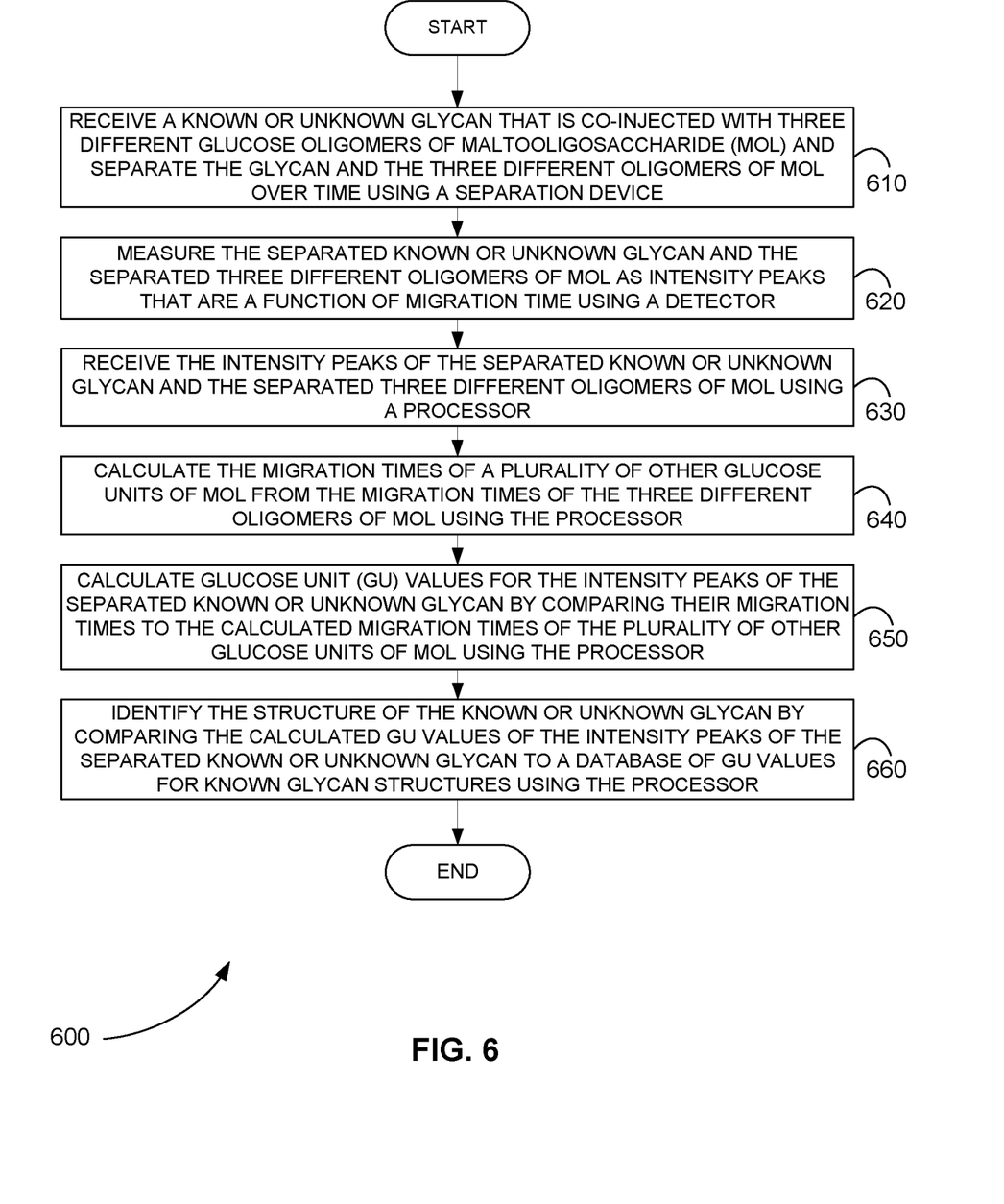
FIG. 6 is a flowchart showing a method for identifying the structure of a glycan by co-injecting with the glycan a triple internal standard made up of three different oligomers of MOL, in accordance with various embodiments.

FIG. 6 is a flowchart showing a method 600 for identifying the structure of a glycan by co-injecting with the glycan a triple internal standard made up of three different oligomers of MOL, in accordance with various embodiments.

In step 610 of method 600, a known or unknown glycan and three different oligomers of MOL co-injected with the glycan are received and the glycan and the three different oligomers of MOL are separated over time using a separation device. The MOL comprises oligomers that have a degree of polymerization (DP) ranging from unity up to dozens. The ratio of the difference in migration time between two consecutive oligomers of MOL and the difference in migration time between adjacent consecutive oligomers of MOL is a first known constant value in a first region of the DP range of MOL and a second known constant value in a second region of the DP range of MOL. Two of the three different oligomers of MOL are selected to produce migration times in one of the first region or the second region. The third of the three different oligomers of MOL is selected to produce a migration time in the other of the first region or the second region.

In step 620, the separated known or unknown glycan and the separated three different oligomers of MOL are measured as intensity peaks that are a function of migration time using a detector.

In step 630, the intensity peaks of the separated known or unknown glycan and the separated three different oligomers of MOL are received using a processor.

In step 640, the migration times of a plurality of other oligomers of MOL are calculated from the migration times of the three different oligomers of MOL and the first known constant value and the second known constant value using the processor.

In step 650, glucose unit (GU) values for the intensity peaks of the separated known or unknown glycan are calculated by comparing their migration times to the calculated migration times of the plurality of other oligomers of MOL using the processor.

Finally, in step 660, the structure of the known or unknown glycan is identified by comparing the calculated GU values of the intensity peaks of the separated known or unknown glycan to a database of GU values for known glycan structures using the processor.

Computer Program Product for Identifying a Glycan

In various embodiments, computer program products include a tangible computer-readable storage medium whose contents include a program with instructions being executed on a processor so as to perform a method for identifying the structure of a glycan by co-injecting with the glycan a triple internal standard made up of three different oligomers of MOL. This method is performed by a system that includes one or more distinct software modules.

Figure 7:
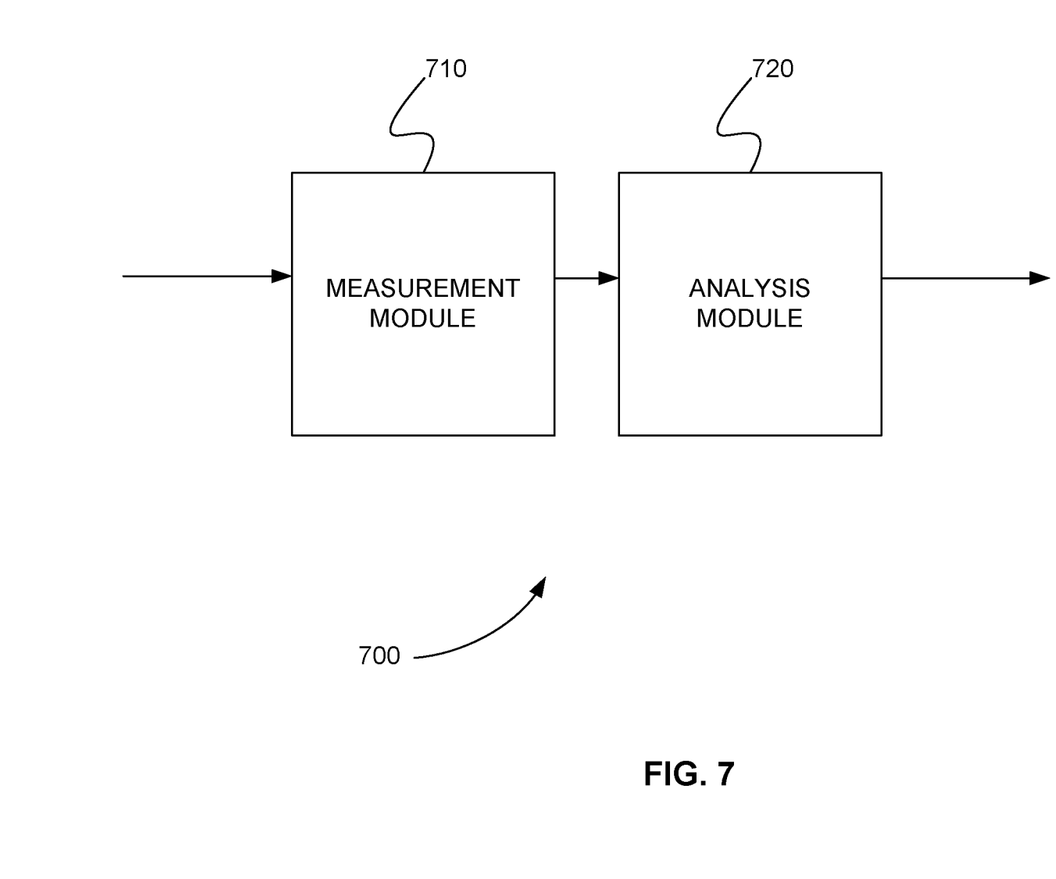
FIG. 7 is a schematic diagram of a system that includes one or more distinct software modules that performs a method for identifying the structure of a glycan by co-injecting with the glycan a triple internal standard made up of three different oligomers of MOL, in accordance with various embodiments.

FIG. 7 is a schematic diagram of a system 700 that includes one or more distinct software modules that perform a method for identifying the structure of a glycan by co-injecting with the glycan a triple internal standard made up of three different oligomers of MOL, in accordance with various embodiments. System 700 includes measurement module 710 and analysis module 720.

Measurement module 710 instructs a separation device to receive a known or unknown glycan that is co-injected with three different oligomers of MOL and to separate the glycan and the three different oligomers of MOL over time. MOL includes oligomers that have a degree of polymerization (DP) ranging from unity up to dozens. The ratio of the difference in migration time between two consecutive oligomers of MOL and the difference in migration time between adjacent consecutive oligomers of MOL is a first known constant value in a first region of the DP range of MOL and a second known constant value in a second region of the DP range of MOL. Two of the three different oligomers of MOL are selected to produce migration times in one of the first region or the second region. The third of the three different oligomers of MOL is selected to produce a migration time in the other of the first region or the second region.

Measurement module 710 instructs a detector to measure the separated known or unknown glycan and the separated three different oligomers of MOL as intensity peaks that are a function of migration time.

Analysis module 720 receives the intensity peaks of the separated known or unknown glycan and the separated three different oligomers of MOL. Analysis module 720 calculates the migration times of a plurality of other oligomers of MOL from the migration times of the three different oligomers of MOL and the first known constant value and the second known constant value. Analysis module 720 calculates glucose unit (GU) values for the intensity peaks of the separated known or unknown glycan by comparing their migration times to the calculated migration times of the plurality of other oligomers of MOL using the analysis module. Finally, analysis module 720 identifies the structure of the known or unknown glycan by comparing the calculated GU values of the intensity peaks of the separated known or unknown glycan to a database of GU values for known glycan structures.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying the structure of a glycan by co-injecting with the glycan a triple internal standard made up of three different glucose α1-4 oligomers of maltooligosaccharide (MOL), comprising:
    a separation device that receives a known or unknown glycan that is co-injected with three different oligomers of MOL and separates the glycan and the three different oligomers of MOL over time, wherein MOL comprises oligomers that have a degree of polymerization (DP) ranging from unity up to dozens, wherein the ratio of the difference in migration time between two consecutive oligomers of MOL and the difference in migration time between adjacent consecutive oligomers of MOL is a first known constant value in a first region of the DP range of MOL and a second known constant value in a second region of the DP range of MOL, and wherein two of the three different oligomers of MOL are selected to produce migration times in one of the first region or the second region and the third of the three different oligomers of MOL is selected to produce a migration time in the other of the first region or the second region;
    a detector that measures the separated known or unknown glycan and the separated three different oligomers of MOL as intensity peaks that are a function of migration time; and
    a processor that
        receives the intensity peaks of the separated known or unknown glycan and the separated three different oligomers of MOL,
        calculates the migration times of a plurality of other oligomers of MOL from the migration times of the three different oligomers of MOL producing a virtual ladder of migration times for oligomers of MOL and the first known constant value and the second known constant value,
        calculates glucose unit (GU) values for the intensity peaks of the separated known or unknown glycan by comparing their migration times to the calculated migration times of the virtual ladder of migration times for oligomers of MOL, and identifies the structure of the known or unknown glycan by comparing the calculated GU values of the intensity peaks of the separated known or unknown glycan to a database of GU values for known glycan structures.

2. The system of claim 1, wherein the separation device comprises a capillary electrophoresis (CE), or multicapillary electrophoresis device.

3. The system of claim 1, wherein the separation device comprises a liquid chromatography (LC) device.

4. The system of claim 1, wherein the known or unknown glycan and the three different oligomers of MOL are labeled for laser-induced fluorescence (LIF) before co-injection and the detector comprises an LIF detector.

5. The system of claim 1, wherein the detector comprises an ultraviolet (UV) light detector.

6. The system of claim 1, wherein the detector comprises a mass spectrometer.

7. The system of claim 1, wherein the three different oligomers of MOL comprise maltose (lower bracketing standard), maltotriose (internal standard), and maltopentadecaose (upper bracketing standard).

8. The system of claim 1, wherein the first region of the DP range of MOL comprises DP values $\geq$DP2 and $\leq$DP7 and the second region of the DP range of MOL comprises DP values $\geq$DP7.

9. The system of claim 1, wherein the two of the three different oligomers of MOL are selected to produce migration times in the first region and the third of the three different oligomers of MOL is selected to produce a migration time in the second region.

10. The system of claim 1, wherein the two of the three different oligomers of MOL are selected to produce migration times in the second region and the third of the three different oligomers of MOL is selected to produce a migration time in the first region.

11. A method for identifying the structure of a glycan by co-injecting with the glycan a triple internal standard made up of three different oligomers of maltooligosaccharide (MOL), comprising:
    receiving a known or unknown glycan that is co-injected with three different oligomers of MOL and separating the glycan and the three different oligomers of MOL over time using a separation device, wherein MOL comprises oligomers that have a degree of polymerization (DP) ranging from unity up to dozens, wherein the ratio of the difference in migration time between two consecutive oligomers of MOL and the difference in migration time between adjacent consecutive oligomers of MOL is a first known constant value in a first region of the DP range of MOL and a second known constant value in a second region of the DP range of MOL, and wherein two of the three different oligomers of MOL are selected to produce migration times in one of the first region or the second region and the third of the three different oligomers of MOL is selected to produce a migration time in the other of the first region or the second region;
    measuring the separated known or unknown glycan and the separated three different oligomers of MOL as intensity peaks that are a function of migration time using a detector;
    receiving the intensity peaks of the separated known or unknown glycan and the separated three different oligomers of MOL using a processor;
    calculating the migration times of a plurality of other oligomers of MOL from the migration times of the three different oligomers of MOL producing a virtual ladder of migration times for oligomers of MOL and the first known constant value and the second known constant value using the processor;

calculating glucose unit (GU) values for the intensity peaks of the separated known or unknown glycan by comparing their migration times to the calculated migration times of the virtual ladder of migration times for oligomers of MOL using the processor; and identifying the structure of the known or unknown glycan by comparing the calculated GU values of the intensity peaks of the separated known or unknown glycan to a database of GU values for known glycan structures using the processor.

12. The method of claim 11, wherein the three different oligomers of MOL comprise maltose, maltotriose, and maltopentadecaose.

13. The method of claim 11, wherein the two of the three different oligomers of MOL are selected to produce migration times in the first region and the third of the three different oligomers of MOL is selected to produce a migration time in the second region.

14. The method of claim 11, wherein the two of the three different oligomers of MOL are selected to produce migration times in the second region and the third of the three different oligomers of MOL is selected to produce a migration time in the first region.

15. A computer program product, comprising a non-transitory tangible computer-readable storage medium whose contents include a program with instructions being executed on a processor so as to perform a method for identifying the structure of a glycan by co-injecting with the glycan a triple internal standard made up of three different oligomers of maltooligosaccharide (MOL), comprising:

providing a system, wherein the system comprises one or more distinct software modules, and wherein the distinct software modules comprise a measurement module and an analysis module;

instructing a separation device to receive a known or unknown glycan that is co-injected with three different oligomers of MOL and to separate the glycan and the three different oligomers of MOL over time using the measurement module, wherein MOL comprises oligomers that have a degree of polymerization (DP) ranging from unity up to dozens, wherein the ratio of the difference in migration time between two consecutive oligomers of MOL and the difference in migration time between adjacent consecutive oligomers of MOL is a first known constant value in a first region of the DP range of MOL and a second known constant value in a second region of the DP range of MOL, and wherein two of the three different oligomers of MOL are selected to produce migration times in one of the first region or the second region and the third of the three different oligomers of MOL is selected to produce a migration time in the other of the first region or the second region;

instructing a detector to measure the separated known or unknown glycan and the separated three different oligomers of MOL as intensity peaks that are a function of migration time using the measurement module;

receiving the intensity peaks of the separated known or unknown glycan and the separated three different oligomers of MOL using the analysis module;

calculating the migration times of a plurality of other oligomers of MOL from the migration times of the three different oligomers of MOL producing a virtual ladder of migration times for oligomers of MOL and the first known constant value and the second known constant value using the analysis module;

calculating glucose unit (GU) values for the intensity peaks of the separated known or unknown glycan by comparing their migration times to the calculated migration times of the virtual ladder of migration times for oligomers of MOL using the analysis module; and identifying the structure of the known or unknown glycan by comparing the calculated GU values of the intensity peaks of the separated known or unknown glycan to a database of GU values for known glycan structures using the analysis module.

* * * * *